United States Patent [19]

Wang

[11] Patent Number: 4,855,407
[45] Date of Patent: Aug. 8, 1989

[54] SOLID PHASE PROCESS FOR SYNTHESIZING PEPTIDES

[75] Inventor: Su S. Wang, Belmont, Calif.

[73] Assignee: Alpha-1 Biomedicals, Inc., Washington, D.C.

[21] Appl. No.: 849,835

[22] Filed: Apr. 9, 1986

Related U.S. Application Data

[63] Continuation-in-part of Ser. No. 722,218, Apr. 11, 1985, abandoned.

[51] Int. Cl.$^4$ .................... C07C 103/52; A61K 37/02
[52] U.S. Cl. .................... 530/334; 525/54.1; 530/324
[58] Field of Search ............... 525/54.1; 530/334, 301, 530/324, 334, 335, 336

[56] References Cited

U.S. PATENT DOCUMENTS

| | | | |
|---|---|---|---|
| 4,148,788 | 4/1979 | Wang | 530/324 |
| 4,207,311 | 6/1980 | Brown et al. | 530/327 |
| 4,229,438 | 10/1980 | Fujino et al. | 530/328 |
| 4,244,946 | 1/1981 | Rivier et al. | 514/15 |
| 4,382,922 | 5/1983 | Rivier et al. | 530/313 |
| 4,406,832 | 9/1983 | Mills | 530/330 |
| 4,478,984 | 10/1984 | Bryan | 525/333.6 |
| 4,507,230 | 3/1985 | Tam et al. | 530/334 |

FOREIGN PATENT DOCUMENTS 2212787  10/1972  Fed. Rep. of Germany .

OTHER PUBLICATIONS

J. Org. Chem, vol. 50, No. 25, 12/13/85, pp. 5291–5298. American Chemical Society, J. P. Tan, "A Gradative Deprotection Strategy for the Solid-Phase synthesis of Peptide Amides Using p-(acyloxy)benzhydroylamine Resin and the $S_N 2$ Deprotection Method".
Chemische Berichte, vol. 103, No. 7, 1970, pp. 2041–2051, Verlag Chemie GmbH, Weinheim, DE; W. Konig, et al., "Eine neue Amid–Schutzgruppe".
Helvetica Chimica Acta, vol. 54, Fasc. 8, 1971, pp. 2772–2775, P. Rivaille, et al., "Synthese en phase solide de l'hormone de liberation de l'hormone luteotrophique (LH–RH)".
Chemical Communications, (The Journal of the Chemical Society, Section D), No. 11, 6/10/70, pp. 650–651, P. G. Pietta, et al., "Amide Protection and Amide Supports in Solid-Phase Peptide Synthesis".

*Primary Examiner*—Morton Foelak
*Assistant Examiner*—Nathan M. Nutter
*Attorney, Agent, or Firm*—Sherman and Shalloway

[57] ABSTRACT

Thymosin $\alpha 1$ and other peptide amides are synthesized in the solid phase using methylbenzhydrylamine resin as the support and hydrogen bromide as the deprotecting and cleaving agents. The N-terminal 14 amino acid partial sequence of thymosin $\alpha 1$, Ac-Ser-Asp-Ala-Ala-Val-Asp-Thr-Ser-Ser-Glu-Ile-Thr-Thr-Lys-OH is synthesized on benzyl ester resin. Using a mixture of hydrogen bromide, anisole and thioanisole as the cleavage and deprotection composition, the yields of the cleaved peptide and the selectivity of the deprotection is highly improved. For example, yields of thymosin $\alpha 1$ have been increased by about 90% as compared to the use of hydrogen bromide alone. By using hydrogen bromide rather than hydrogen fluoride, the synthesis can use conventional laboratory glassware and the synthesis can be easily scaled up to commercial production.

21 Claims, No Drawings

SOLID PHASE PROCESS FOR SYNTHESIZING PEPTIDES

This is a continuation-in-part of prior application Ser. No. 722,218, filed Apr. 11, 1985 now abandoned.

BACKGROUND OF THE INVENTION

1. Field of Invention

This invention relates to an improved process for synthesis of peptides by the solid phase method. More particularly, the invention relates to the synthesis of peptide amides by solid phase peptide synthesis using a novel resin support, methylbenzhydrylamine resin, and hydrogen bromide as the cleavage and deprotecting agent for separating the resin-bound peptide from the resin support. In a particular aspect, the invention relates to the solid phase synthesis of thymosin $\alpha_1$. The invention also relates to an improved process for synthesizing peptides, and particularly, thymosin $\alpha_1$ and the thymosin $\alpha_1$-$N_{1-14}$ fragment, by solid phase synthesis using an improved cleavage/deprotecting composition, namely hydrogen bromide with a mixture of anisole and thioanisole.

2. Description of the Prior Art

The function of peptides in human health has received much recognition in recent years, see e.g. "Peptides: A Medical Rediscovery" by Joseph Alper, High Technology, Vol. 3, No. 9, September 1983, pages 60–63. Peptides have been shown to function, for example, as hormones for regulating growth, reproduction, and immunology, and as neurotransmitters. While actual and positive biological results have been observed for several dozens of different peptides, still much work remains to be done to determine how the petides work in the body. For this purpose, large quantities of the peptides are required. Also, in order for the peptides of known biological activity to be of practical significance in health care, they must be made readily available in large quantities and at relatively low cost.

In addition to the "natural" peptides, i.e. those produced in the body, "synthetic" peptides or analogs, which may be considered as derivatives of natural peptides, but having one or more chemical modifications in the molecular structure of the natural peptide, are also valuable for their modified chemical properties, such as resistance to enzyme degradation. Here again, the availability of relatively inexpensive means to rapidly and inexpensively produce synthetic peptides would be highly valuable.

Presently, various procedures for synthesizing peptides, i.e. for formation of a peptide linkage between amino acids, are known. Conventional procedures include both solution-phase (or liquid phase) methods and solid-phase methods. A general discussion of peptide synthesis can be found, for example, in Schroder E. Lubke: "The Peptides," Vol. 1 (1966), Academic Press, New York, U.S.A, and Neurath and Hill, "The Proteins," Vol. 2 (1976), Academic Press, New York, U.S.A. Generally, these procedures involve the reaction between the free amino group of an amino acid or residue thereof having its carboxyl group, hydroxyl group or other reactive group(s) protected, and the free primary carboxylic group of another amino acid or residue thereof having its amino group or other reactive group(s) protected to form a peptide bond. Each amino acid in the desired sequence can be added singly successively to another amino acid or residue thereof or separate peptide fragments with the desired amino acid sequence can be synthesized and then condensed to provide the desired peptide.

In the past ten to twenty years the synthesis of peptides has been simplified by utilizing the solid phase synthesis method according to the general principles developed by Merrifield, [R. B. Merrifield, J. Am. Chem. Soc. 85, 2149–2154 (1963); Stewart, et al, Solid Phase Peptide Synthesis, Freeman & Co., San Francisco, CA (1969); Barany, et al, The Peptides, Analysis, Synthesis and Biology, Vol. 2, pages 1–284, (1980)]. Briefly in solid-phase peptide synthesis (SPPS), the carboxyl group of the first amino acid in a peptide is chemically bound to the surface of tiny, insoluble beads, with the other reactive sites on the amino acid being temporarily blocked. The amino acid-bound resin beads are placed in a reaction vessel and unbound acid is washed away. After chemically unblocking the reactive amino group, the next amino acid in the desired sequence of the object peptide is added with a chemical coupling agent such that the two acids bind together, via a peptide bond. The synthesis is continued by repeating the foregoing process with successive amino acids in the sequence being added one at a time until the total peptide sequence is built up on the resin. Upon completion of the desired peptide sequence, the protected peptide is cleaved from the resin support, and all protecting groups are removed. The cleavage reaction and removal of protecting groups may be accomplished simultaneously or sequentially.

SPPS has recently been adapted to automated and computerized instrumentation offering substantial improvements in speed, efficiency, and reliability. However, the use of such instrumentation has been substantially limited to production of peptides on a relatively small scale, on the order of a few milligrams per production cycle. Also, the procedure inherently results in the production of unwanted by-products, unreacted acids, solvents, coupling or decoupling agents, cleavage products and so on, making the subsequent purification procedures troublesome.

Although the art is aware of various different materials used as the insoluble beads, including glass, silica, synthetic resins, etc., the synthetic resins are most commonly used as the support material (insoluble beads). Conventional materials used as the resin include the styrene-divinyl benzene resin modified with a reactive group, such as chloromethylated styrene-divinyl benzene resin and benzhydrylamine resin (BHA). BHA is particularly useful for synthesis of peptide amides, i.e. peptides of which the C-terminal amino acid has a carboxylamide ($-CONH_2$) group, since the amide group can be formed directly. The benzhydrylaminopolystyrenedivinyl benzene resin support is described by P. Rivaille, et al, Helv. Chim. Acta., 54, 2772 (1971).

Hydrogen fluoride, HF, is commonly used as the cleavage agent, and also as the deprotecting agent for removing the various blocking groups.

Unfortunately, HF, whether in liquid, anhydrous, or gaseous form, is highly corrosive and toxic requiring special handling and special plastic materials. As a result, the scale-up of the SPPS procedure from the laboratory scale to commercial scale production (e.g. on the order of one or more grams per production run) has proven extremely difficult.

It has been known to use the less corrosive and less toxic hydrogen bromide (HBr) is place of HF as the cleavage agent, alone, or together with anisole as a catalyst for cleaving the bound protected peptide from the supporting resin. However, HBr alone or with anisole does not function effectively as a cleavage agent with BHA resin, apparently due to the relatively high acid stability of BHA resin.

Accordingly, there is a great need to provide a method whereby peptides can be produced economically and simply using chemical substances which are non-corrosive to ordinary laboratory glasswares and of relatively low toxicity and which can produce the peptides on a commercial scale.

OBJECTS OF THE INVENTION

Therefore, it is an object of this invention to provide a safe, simple method for producing peptides by the solid phase peptide synthesis method which avoids the use of highly corrosive and toxic hydrogen fluoride.

It is another object to produce peptides according to the SPPS method which can be scaled up to commercial scale production, and which uses ordinary laboratory glassware, plastics, etc., for handling, storing, and transporting all of the chemicals required for the process, including the cleavage and deprotecting agent.

Still another object of the invention is the production of peptides by the SPPS method in which the cleavage step results in less side reactions and produces fewer unwanted by-products, thereby greatly simplifying the subsequent purification step(s).

A further object of the invention is to provide a solid phase peptide synthesis method in which the yield of peptide at the cleavage step is improved over the conventional processes using HF or HBr with anisole.

A specific object of this invention is to provide an improved process for synthesizing thymosin $\alpha_1$ by solid phase peptide synthesis using HBr as the cleavage and deprotecting agent for synthesizing thymosin $\alpha_1$ and thymosin $\alpha_1$-$N_{1-14}$ fragment by solid phase peptide synthesis.

SUMMARY OF THE INVENTION

These and other objects of the invention which will become apparent from the following detailed description and specific embodiments are provided by a method for synthesizing peptide amides having the amino acid sequence represented by the formula $Y_p$—X—NH$_2$, where $Y_p$ represents the N-terminal peptide fragment and X—NH$_2$ represents the C-terminal amino acid having an amide group (—CONH$_2$) in its molecular structure in the solid phase wherein hydrogen bromide is used as a deprotecting and cleaving agent and methylbenzhydrylamine resin is used as the solid support. In accordance with a preferred embodiment of the invention, the cleavage step is carried out in trifluoroacetic acid in the presence of anisole. In accordance with a more preferred embodiment of the invention, the cleavage step is carried out in the presence of a mixture of anisole and thioanisole whereby the yields of peptide are substantially improved and production of unwanted by-products substantially reduced.

In another aspect of the invention, which is broadly applicable to the solid phase peptide synthesis for producing a peptide of a desired amino acid sequence by the steps of (a) temporarily chemically protecting the reactive amino group and any other reactive groups, other than the carboxylic acid group at the alpha-position, on the C-terminal amino acid of the peptide;

(b) chemically bonding the protected C-terminal amino acid via the carboxylic acid (—COOH) group thereof to a resin support;

(c) chemically deprotecting the reactive amino group of the resin-bound protected amino acid;

(d) chemically coupling via a peptide bond the next amino acid in the desired sequence by contacting the resin-bound amino acid from step (c) with said next amino acid having all of the reactive groups thereof, other than the carboxylic acid group at the alpha-position, chemically protected, in the presence of a coupling agent;

(e) chemically deprotecting the reactive amino group of the coupled amino acid from step (d);

(f) continuing the synthesis by repeating steps (d) and (e) with successive amino acids in the desired sequence being added one at a time until the total desired sequence of the protected peptide is built up on the resin, and (g) cleaving the protected peptide from the resin support and deprotecting the protected side chain reactive groups;

the yield of the cleaved and deprotected peptide is increased by contacting the resin supported-protected peptide in step (g) with a cleavage and deprotecting composition which includes a mixture of hydrogen bromide, anisole and thioanisole.

In a specific embodiment, the present invention provides a method of synthesizing thymosin $\alpha_1$ in the solid phase wherein hydrogen bromide, rather than the highly corrosive hydrogen fluoride, is used as a deprotecting and cleaving agent and methylbenzhydrylamine resin is used as solid support. In this specific embodiment also, by using a mixture of anisole and thioanisole in the deprotecting and cleaving mixture, the yield of thymosin $\alpha_1$ is substantially improved.

DETAILED DESCRIPTION OF THE INVENTION

Although it has long been known to use hydrogen bromide as the cleavage agent for cleaving the peptide-resin bond in the solid phase protein synthesis method the use of HBr has been limited to certain resin supports, primarily chloromethylated polystyrene-divinylbenzene; HBr does not, however, effectively function as the cleavage or deprotecting agent with benzhydrylamine resin.

The present invention is based on the surprising discovery that by using methylbenzhydrylamine resin as the resin support the cleavage of the bound peptide from the support can be performed using hydrogen bromide as the cleaving agent with a high yield and high degree of specificity of cleavage and deprotecting, not possible with benzhydrylamine resin. Furthermore, the yield of peptide is substantially increased when the deprotecting and cleavage with HBr is carried out in the presence of anisole and still further improvements are achieved according to the present invention by using a mixture of anisole and thioanisole.

Details of the invention will be described below in connection with the production of thymosin $\alpha_1$. It should be understood, however, that the methylbenzhydrylamine resin support can be used in the production of any peptide the C-terminal amino acid of which includes an amide radical group, such as aspargine (Asn) ($\alpha$-aminosuccinamic acid)

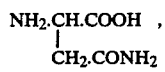

and glutamine (Gln),

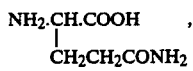

or generally, any amino acid in which the carboxylic acid group is modified to an amide group. An example of a peptide falling in the latter group is the calcitonin peptide in which the N-terminal (position 32) amino acid is Pro.NH$_2$, i.e.

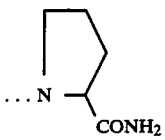

where ... represents the residue of the peptide at positions 1-31 (see e.g. U.S. Pat. No. 4,217,268 for a disclosure of the complete structure of calcitonin and its des-X$^2$ derivatives, as well as the solid phase synthesis thereof using benzhydrylamine resin support and HF cleavage/deprotection). In general, any peptide which can be produced by solid phase synthesis or benzhydrylamine (BHA) resin support can be produced with the methylbenzhydrylamine (MBHA) resin support according to the present invention. In addition to thymosin $\alpha_1$ and calcitonin mentioned above, representative of other known peptides which can be produced by the improved procedure of this invention include oxytocin, vasopressin, LH-RH antagonists (see e.g. U.S. Pat. No. 4,431,635, U.S. Pat. No. 4,530,920), the glutamine (Gln) terminated synthetic hormone-like peptides disclosed in U.S. Pat. No. 4,389,342, etc. Also, fragments of peptide which have the —CONH$_2$ groups can be synthesized by the solid phase synthesis method using MBHA resin support and HBr cleavage. For instance, mention can be made, for example, of the biologically active peptides which are fragments of the sauvagine peptide disclosed in U.S. Pat. No. 4,474,765; fragment 521: Ala-Ser-Pro-Ser.Gln of the Fc region of immunoglobulin E (IgE) useful in blocking mammalian allergic reaction (disclosed in U.S. Pat. No. 4,161,522); peptide fragments of formulas (VI), (VII), (IX), (X), (XI), (XV) and (SVI) of U.S. Pat. No. 4,497,801, etc.

Accordingly, it should be understood that the improved solid phase peptide synthesis of this invention is applicable to the production of any peptide having an amide (—CONH$_2$) radical as part of the C-terminal amino acid whether in the form of a "naturally" occurring amino acid, e.g. aspargine (Asn) or glutamine (Gln) or as an amino-group substituted amino acid, the amino-group substituent replacing the hydroxyl group of a carboxylic acid radical. Thus, the peptides produced by the improved SPPS method of this invention may be generally referred to as peptide amides and may be represented by the formula $Y_p$—X—NH$_2$ where $Y_p$ represents the N-terminal peptide fragment and X—NH$_2$ represents the C-terminal amino acid having an amide group (—CONH$_2$).

It is understood that peptide sequences are written according to the generally accepted convention whereby the N-terminal amino acid is on the left and the C-terminal amino acid is on the right. The N-terminal peptide fragment $Y_p$ will have at least two, preferably at least 3, amino acids bonded together by peptide bonds, —CONH—. There is no particular upper limit to the number of amino acids in the $Y_p$ peptide fragment. For instance, it is possible to use SPPS methodology to synthesize peptides containing as many as 40 or more amino acids, and polypeptides containing, for example, up to about 50 or 60 or more amino acids can be synthesized. In the C-terminal amino acid represented by X—NH$_2$, X may be any of the well known and reasonably accessible amino acids as described, for example, in general textbooks on peptide chemistry; for instance, see K. D. Kopple, "Peptides and Amino Acids," W. A. Benjamin, Inc., New York, 1966, pp. 4-7. Furthermore, the optically active amino acids may be in either the D-, L-, or DL-form.

The methylbenzhydrylamine resin used in the subject invention is prepared from commercially available polystyrene resin beads (1% divinyl benzene, 200-400 mesh U.S. Standard) by reacting the same with p-toluoyl chloride in the presence of a Lewis acid such as aluminum chloride in an inert solvent such as dichloroethane at a low temperature, preferably 0° to 5° C. to form a p-toluoyl resin, CH$_3$—C$_6$H$_4$—CO—C$_6$H$_4$-resin. This resin is reacted with a mixture of ammonium formate, formamide and formic acid at reflux temperature (160°-170° C.) for 24 hours to yield N-formyl methylbenzhydrylamine resin, CH$_3$—C$_6$H$_4$—CH(N-H—CO—H)—C$_6$H$_4$-resin. Upon hydrolysis in dilute hydrochloric acid, the desired methylbenzhydrylamine resin, i.e. CH$_3$—C$_6$H$_4$—CH(NH$_2$.HCl)—C$_6$H$_4$-resin, is formed.

According to a specific embodiment of the invention, thymosin $\alpha_1$ having the following sequence AC—Ser—Asp—Ala—Ala—Val—Asp—Thr—Ser—Ser—

Glu—Ile—Thr—Thr—Lys—Asp—Leu—Lys—Glu—Lys—

Lys—Glu—Val—Val—Glu—Glu—Ala—Glu—Asn—OH is produced by solid phase peptide synthesis using the so-produced methylbenzhydrylamine resin.

The methylbenzhydrylamine resin so formed is neutralized and acylated with N$\alpha$-Boc-$\alpha$-benzyl-L-aspartic acid in the presence of dicyclohexylcarbodiimide to give Boc-asparaginyl resin. The solid phase synthesis is then continued by the sequential incorporation of one amino acid unit in each cycle to form a peptide unit which is acetylated to give an acetylated octacosapeptide resin of the structure:

Ac—Ser(Bzl)—Asp(OBzl)—Ala—Ala—Val—Asp(OBzl)—

Thr(Bzl)—Ser(Bzl)—Ser(Bzl)—Glu(OBzl)—Ile—Thr(Bzl)—

Thr(Bzl)—Lys(ClZ)—Asp(OBzl)—Leu—Lys(ClZ)—

Glu(OBzl)—Lys(ClZ)—Lys(ClZ)—Glu(OBZl)—Val—Val—

Glu(OBzl)—Glu(OBzl)—Ala—Glu(OBzl)—Asp(NH—

-continued

CH(C₆H₄—CH₃)—C₆H₄—resin)-OBzl.

The protected thymosin α₁-resin so obtained is suspended in trifluoroacetic acid and treated with dry hydrogen bromide gas at ordinary temperature (20°-25° C.) for about one hour in order to cleave the polypeptide from the resin and at the same time remove all the protecting groups from the side chains of the amino acid residues. Although hydrogen bromide may be used alone it is preferred to include anisole and, most preferably, a mixture of anisole and thioanisole in the trifluoroacetic acid when treating with dry hydrogen bromide gas. The present inventor has found that when a mixture of HBr, TFA and anisole is used as the deprotecting and cleaving mixture, the yield of thymosin α₁ is increased by about 50% over the instance when a mixture of only TFA and HBr is used. When a mixture of HBr, TFA, anisole and thioanisole is used, the yield is improved by about 90%. The volume ratio of anisole:-thioanisole is preferably from about 20:80 to about 80:20, most preferably about 50:50 (i.e. about 1:1).

The excess acids are then evaporated off at 40° C. under partial vacuum and the anisole and thioanisole are washed off with ether. Crude thymosin α₁ is extracted from the residue with 1% ammonium acetate and desalted on a Sephadex G-10 column using 0.1N acetic acid as the eluent. Thereafter, the thymosin α₁ may be purified by high pressure liquid chromatography (C₁₈ reversed phase column, 5.7×30 cm). When subjected to analytical high pressure liquid chromatography, the so obtained thymosin α₁ behaves identically to reference thymosin α₁ prepared by the fragment condensation method. Moreover, the presently synthesized thymosin α₁ has been found indistinguishable from natural thymosin α₁ and gives satisfactory amino acid analysis.

It is noted that the combination of methylbenzhydrylamine resin and hydrogen bromide must be used in order to obtain the desired results. If benzhydrylamine resin were used as the support resin, hydrogen fluoride must be used in the deprotecting and cleaving step. This represents a significant difference between the method described in U.S. Pat. No. 4,148,788 disclosing the SPPS method for producing thymosin α₁ and the present invention.

In the description above and following, the abbreviations have the following meaning according to standard customary nomenclature:

Boc, t-butyloxycarboxy; Bzl, benzyl; DCC, dicyclohexylcarbodiimide; Z, benzyloxycarbonyl; TFA, trifluoroacetic acid, and ClZ, 2-chlorobenzyloxycarbonyl.

While specific protecting groups have been employed in describing the preferred embodiment for synthesis of thymosin α₁, it is within the skill of the art to utilize equivalent conventional protecting groups.

For example, —Ser(R¹) is utilized as the protected form of serine wherein R¹ is a conventional protecting group for the hydroxyl group of the serine residues such as benzyl, acetyl, benzoyl, tert-butyl, trityl, 4-bromobenzyl, 2,6-dichlorobenzyl and benzyloxycarbonyl; —Asp—(OR²) is utilized as the protected form of aspartic acid wherein R² is a conventional protecting group for carboxyl groups selected from esters such as aryl esters, particularly phenyl or phenyl substituted with lower alkyl, halo, nitro, thio or substituted thio, i.e., methylthio, aralkyl esters such as benzyl or benzyl substituted with methoxy, halo or nitro, lower alkyl esters such as methyl, ethyl, tert-butyl and tert-amyl, substituted lower alkyl esters such as 2-haloethyl β,β-dimethylaminoethyl and cyanomethyl, benzhydryl esters and phenacyl esters; —Thr(R¹)— is utilized as the protected form of threonine wherein R¹ is as defined above; —Glu(OR²)— is utilized as the protected form of glutamic acid wherein R² is as defined above; —Lys(R³) is utilized as the protected form of lysine wherein R³ is a conventional ω-amino protecting group selected from benzyloxycarbonyl which may be optionally substituted in the aromatic ring such as by 2-chloro, 4-chloro, 2-bromo, 4-bromo, 2,4-dichloro, 4-nitro, 4-methoxy, 3,5-dimethoxy, 4-methyl, 2,4,6-trimethyl, 4-phenylazo, 4-(4-methoxyphenylazo), 2-(N,N-dimethylcarbonamido), 4-dihydroxyboryl, and 2-nitro-4,5-dimethoxy, other urethane type protecting groups, such as 4-toluenesulfonylethyloxycarbonyl, 9-fluorenylmethyloxycarbonyl and related base cleavable groups, cyclopentyloxycarbonyl and related nitrogen containing urethane groups; acyl groups such as formyl, trifluoroacetyl, phthaloyl, benzenesulfonyl, acetoacetyl, chloroacetyl, 2-nitrobenzoyl, 4-toluene-sulfonyl; and —Asp—OR² is utilized as the protected form of asparagine wherein R² is as defined above.

Although the above description has been given with particular emphasis for the solid phase peptide synthesis of thymosin α₁, with its specified amino acid sequence and specified protected side chain groups, the practitioner will readily recognize that certain general conditions will preferably be selected regardless of the particular peptide being synthesized. For example, it is well recognized that the α-amino group of each amino acid employed in the peptide synthesis must be protected during the coupling reaction to prevent side reactions involving the reactive α-amino function. Similarly, for those amino acids containing reactive side-chain functional groups (e.g. sulfhydryl, ε-amino, hydroxyl, carboxyl), such functional groups need also be protected both during the initial coupling of the amino acid containing the side-chain group and during the coupling of subsequent amino acid. Suitable protecting groups are known in the art [See for example, *Protective Groups in Organic Chemistry*, M. McOmie, Editor, Plenum Press, N.Y., 1973.]

In selecting a particular protect group, the following conditions must be observed: an α-amino protecting group must: (1) be stable and render the α-amino function inert under the conditions employed in the coupling reaction, and (2) must be readily removable after the coupling reaction under conditions that will not remove the side chain protecting groups or alter the structure of the peptide fragment. A side chain protecting group must: (1) be stable and render the side chain functional group inert under the conditions employed in the coupling reaction, (2) be stable under the conditions employed in removing the α-amino protecting group and (3) be readily removable upon completion of the desired amino acid sequence under reaction conditions that will not alter the structure of the peptide chain, or racemization of any of the chiral centers contained therein. Suitable protecting groups for the α-amino function are t-butyloxycarbonyl (Boc), benzyloxycarbonyl (Cbz), biphenylisopropyloxycarbonyl, t-amyloxycarbonyl, isobornyloxycarbonyl, 1,1-dimethyl-3,5-dimethoxybenzyloxycarbonyl, o-nitrophenylsulfenyl, 2-cyano-t-butyloxycarbonyl, 9-flourenylmethyloxycarbonyl and the like, expecially t-butyloxycarbonyl (Boc).

As examples of carboxyl-protecting groups, there may be mentioned such ester-forming groups as those capable of giving alkyl ester (e.g. methyl, ethyl, propyl,, butyl, t-butyl, etc., esters), benzyl ester, p-nitrobenzyl ester, p-methoxybenzyl ester, p-chlorobenzyl ester, benzhydryl ester, etc. and hydrazide-forming groups such as those capable of giving carbobenzoxy hydrazide, t-butyloxy-carbonyl hydrazide, trityl hydrazide, etc.

As groups for protecting the guanidino group of arginine, there may be mentioned nitro, tosyl, p-methoxybenzenesulfonyl, carbobenzoxy, isobornyloxycarbonyl, admantyloxycarbonyl, etc. The guanidino group may also be protected in the form of a salt with an acid (e.g. benzenesulfonic acid, toluenesulfonic acid, hydrochloric acid, sulfuric acid, etc.).

The hydroxyl group of threonine may be protected, for example, by way of known esterification or etherification. As examples of groups suitable for said esterification, there may be mentioned lower alkanoyl groups (e.g. acetyl), aroyl groups (e.g. benzoyl), and groups derived from carbonic acid, such as benzyloxycarbonyl, ethyloxycarbonyl, etc. As groups suitable for said etherification, there may be mentioned benzyl, tetrahydropyranyl, t-butyl, etc. The hydroxyl group of threonine, however, need not necessarily be protected. Methionine may be protected in the form of a sulfoxide. Other preferred side chain protective groups for particular amino acids include; for tyrosine: benzyl, o-bromobenzyloxycarbonyl, 2,6-dichlorobenzyl, isopropyl, cyclohexyl, cyclopentyl and acetyl; for histidine: benzyl, p-toluenesulfonyl and 2,4-dinitrophenyl; for tryptophan: formyl.

According to the present invention, the production of the peptide amides is carried out using methylbenzhydrylamine (polystyrene-divinyl benzene) resin as the solid support. However, for the production of other types of peptides using the novel HBr, anisole, thioanisole cleavage/deprotecting composition of this invention, other conventional solid supports to which the C-terminal amino acid is attached can be used. Suitable solid supports useful for the solid phase peptide synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer functionalized, crosslinked poly-N-acrylylpyrrolidine resins, and the like, especially chloromethylpolystyrene-1% divinylbenzene polymer.

The $N\alpha$-Boc-amino acid or similarly protected C-terminal amino acid is attached to the methyl benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C., in a solvent such as dichloromethane or DMF, preferably dichloromethane. The attachment to the chloromethyl polystyrenedivinylbenzene type of resin is made by means of the reaction of the $N^1$-protected amino acid, especially the Boc-amino acid, as its cesium, tetramethylammonium, triethylammonium, 4,5-diazabicyclo-[5.4.0]undec-5-ene, or similar salt in ethanol, acetonitrile, N,N-dimethylformamide (DMF), and the like, especially the cesium salt in DMF, with the chloromethyl resin at an elevated temperature, for example, between about 40° and 60° C., preferably about 50° C. for from about 12 to 48 hours, preferably about 24 hours. The removal of the $N^1$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. The coupling of successive protected amino acids can be carried out in an automatic polypeptide synthesizer, as well known in the art. Each protected amino acid is preferably introduced in approximately 2.5 or more molar excess and the coupling may be carried out in dichloromethane, dichloromethane/DMF mixtures, DMF and the like, especially in methylene chloride at about ambient temperature. Other solvents which are known to be useful for the purpose of peptide-forming condensation reaction, for example, dimethylsulfoxide, pyridine, chloroform, dioxane, tetrahydrofuran, ethyl acetate, N-methylpyrrolidone, etc., as well as suitable mixtures thereof may also be used.

The reaction temperature for the condensation/coupling reaction may be selected from the range known to be useful for the purpose of peptide-forming condensation reactions. Thus, it may normally be within the range of about −40° C. to about 60° C., and preferably, about −20° C. to about 0° C. The coupling agent is normally DCC in dichloromethane but may be N,N'-di-iso-propylcarbodiimide or other carbodiimide ether alone or in the presence of HBT, N-hydroxysuccinimide, ethyl 2-hydroxyimino-2-cyanoacetate, other N-hydroxyimides or oximes. Alternatively, protected amino acid active esters (e.g. p-nitrophenyl, pentafluorophenyl and the like) or symmetrical anhydrides may be used.

The coupling, deprotective/cleavage reactions and preparation of derivatives of the polypeptides are suitably carried out at temperatures between about −10° and +50° C., most preferably about 20°–25° C. The exact temperature for any particular reaction will, of course, be dependent upon the substrates, reagents, solvents and so forth, all being well within the skill of the practitioner. The fully deprotected polypeptide may then be purified by a sequence of chromatographic steps employing any or all of the following types: ion exchange on a weakly basic resin in the acetate form; gel permeation chromatography, e.g. on Sephadex G-25; hydrophobic adsorption chromatography on underivatized polystyrene-divinylbenzene (for example, Amberlite XAD); silica gel adsorption chromatography; ion exchange chromatography, e.g. on Sephadex G-25, or countercurrent distribution; high performance liquid chromatography (HPLC), especially reverse phase HPLC on octyl- or octadecylsilyl-silica bonded phase column packing.

In another specific embodiment of the present invention, the N-terminal 14 amino partial sequence of thymosin $\alpha_1$, Ac-Ser-Asp-Ala-Ala-Val-Asp-Thr-Ser-Ser-Glu-Ile-Thr-Thr-Lys-OH (thymosin $\alpha_1$-$N_{1-14}$) is synthesized on benzyl ester resin. The protected thymosin $\alpha_1$-$N_{1-14}$-resin is deprotected and cleaved by treatment with hydrogen bromide, trifluoroacetic acid, anisole and thioanisole in a manner similar to that described above for thymosin $\alpha_1$. Purification of the crude product by preparative high pressure liquid chromatography yields a pure thymosin $\alpha_1$-$N_{1-14}$ compound which is found to be identical to a reference compound synthesized previously by the fragment condensation method in solution.

This invention is further illustrated by the following non-limiting examples.

EXAMPLE 1

Methylbenzhydrylamine Resin 50.9 gm of polystyrene resin beads (copolystyrene-1%-divinyl benzene, 200–400 mesh beads) was suspended in 500 ml of dichloroethane. The mixture was cooled in an ice-bath with gentle mechanical stirring until the temperature went below 5° C.

15.5 g of p-toluoyl chloride and 13.3 g of aluminum chloride were mixed in 250 ml of dichloroethane in a dropping funnel. The solution was added dropwise to the cooled, stirred suspension of the resin beads over a period of about 40 min., care being taken not to allow the reaction to warm up above 5° C. The stirring was continued for 4 hours at room temperature when the resin was washed sequentially with isopropanol, isopropanol-water (1:1 mixture), isopropanol and dried to give 53.8 g of p-toluoyl resin. This resin was then mixed with 168 g of ammonium formate, 201 ml of formamide, 134 ml of formic acid and 350 ml of nitrobenzene. The mixture was gradually heated up to 165°–170° C. under reflux and maintained for 1 day during which time about 115 ml of the aqueous phase was collected into a Dean-Stark trap. The resin was washed and dried as above to yield 55.5 g of N-formyl methylbenzhydrylamine resin. The product was hydrolyzed in a mixture of 300 ml each of 12N HCl and isopropanol under reflux for 3 hr. Washing and drying the resulting resin provided 54.9 g of the hydrochloride form of methylbenzhydrylamine resin. It showed a very strong positive reaction to ninhydrin reagent and incorporated 0.4 mmol of Boc-Ala-OH when neutralized and coupled with Boc-Ala-OH in the presence of dicyclohexylcarbodiimide.

EXAMPLE 2

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH (Thymosin $\alpha_1$)

5.02 gm of methylbenzhydrylamine resin obtained in Example 1 was placed in a peptide synthesis flask equipped with a sintered glass filter at the bottom and a mechanical stirrer at the top. The resin was washed with 20 volumes of 10% triethylamine in methylene chloride and stirred with a fresh portion of the same solution for 10 min. The neutralized methylbenzhydrylamine resin was then reacted with Boc-L-aspartic acid α-benzyl ester (1.95 g, 6 mmol) and dicyclohexylcarbodiimide (1.24 g, 6 mmol) for 2 hours to form Boc-α-benzyl-L-aspartic acyl methylbenzhydrylamine resin. The resin turned from ninhydrin positive to ninhydrin negative after this reaction.

The solid phase peptide synthesis was then continued by performing the following steps wherein in each cycle one amino acid was incorporated sequentially into the growing peptide chain on the resin:

(1) prewash with 40% trifluoroacetic acid in $CH_2Cl_2$;
(2) stir for 28 minutes with 40% trifluoroacetic acid;
(3) three washings with $CH_2Cl_2$;
(4) prewash with 10% triethylamine in $CH_2Cl_2$;
(5) stir for 5 minutes with 10% triethylamine;
(6) wash three times with $CH_2Cl_2$;
(7) stir for 120 minutes with 6 mmol each of Boc-Glu(OBzl)-OH and DCC;
(8) wash once with $CH_2Cl_2$;
(9) wash three times with 50% i-propanol in $CH_2Cl_2$;
(10) wash three times with $CH_2Cl_2$;
(11) test for ninhydrin color reaction; if positive, repeat steps 7–11; if negative, go to the next synthetic cycle.

The synthetic cycle was repeated using the following amino acids sequentially and one at a time in step 7 of each cycle: Boc-Ala-OH, Boc-Glu(OBzl)-OH, Boc-Glu(OBzl)-OH, Boc-Val-OH, Boc-Val-OH, Boc-Glu(OBzl)-OH, Boc-Lys(ClZ)-OH, Boc-Lys(ClZ)-OH, Boc-Glu(OBzl)-OH, Boc-Lys(ClZ)-OH, Boc-Leu-OH, Boc-Leu-OH, Boc-Asp(OBzl)-OH, Boc-Lys(ClZ)-OH, Boc-Thr(Bzl)-OH, Boc-Thr(Bzl)-OH, Boc-Ile-OH, Boc-Glu(OBzl)-OH, Boc-Ser(Bzl)-OH, Boc-Ser(Bzl)-OH, Boc-Thr(Bzl)-OH, Boc-Asp(OBzl)-OH, Boc-Val-OH, Boc-Ala-OH, Boc-Ala-OH, Boc-Asp(OBzl)-OH, Boc-Ser(Bzl)-OH, and $CH_3COOH$. The protected thymosin $\alpha_1$-resin so obtained, Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(Clz)-Asp(OBzl)-Leu-Lys(Clz)-Glu(OBzl)-Lys(ClZ)-Lys(ClZ)-Glu(OBzl)-Val-Val-Glu-Glu(OBzl)-Ala-Glu(OBzl)-Asp(HN—CH($C_6H_4$—$CH_3$)—$C_6H_4$-resin)-OBzl, weighed 16.8 gm. Part (1.01 gm) of this material was mixed with 2 ml each of anisole and thioanisole and 16 ml trifluoroacetic acid. A gentle stream of dry HBr gas was bubbled through the magnetically stirred suspension for 60 minutes at room temperature. The excess acids were then removed by evaporation at 40° C. in a rotary evaporator and the residue washed with ether several times to remove the excess anisole and thioanisole. The peptide was extracted into 1% ammonium acetate (2×25 ml) and the solution desalted on a Sephadex G-10 column (2.6×95 cm) using 0.1M acetic acid as eluant, monitored at 230 nm. The material present in the major peak was lyophilized to give 0.33 g of crude product which on purification on preparative high pressure liquid chromatography ($C_{18}$ reverse phase column, eluted with 10–11.25% $CH_3CN$ in pH 5.0 potassium phosphate buffer) provided 0.10 g of pure thymosin $\alpha_1$. It has the amino acid composition of: Asp, 4.00; Thr, 3.12; Ser, 2.64; Glu, 6.00; Ala, 2.92; Val, 1.92; Ile, 1.04; Leu, 0.96; Lys, 3.98 (hydrolysis in 6N HCl, 110° C., 24 hr). The product migrated identically in analytical HPLC with the reference compound prepared by the fragment condensation method in solution.

EXAMPLE 3

Ac-Ser-Asp-Ala-Ala-Val-Asp-Thr-Ser-Ser-Glu-Ile-Thr-Thr-Lys-OH (Thymosin $\alpha_1$-$N_{1-14}$)

2.0 gm of Boc-Lys(ClZ)-$OCH_2$-$C_6H_4$-resin was placed in a peptide synthesis flask and the solid phase synthesis carried out as described in Example 2, with 3 mmol each of DCC and the following amino acids in step 7 in Example 2 of each cycle: Boc-Thr(Bzl)-OH, Boc-Thr(Bzl)-OH, Boc-Ile-OH, Boc-Glu(OBzl)-OH, Boc-Ser(Bzl)-OH, Boc-Ser(Bzl)-OH, Boc-Thr(Bzl)-OH, Boc-Asp(OBzl)-OH, Boc-Val-OH, Boc-Ala-OH, Boc-Ala-OH, Boc-Asp(OBzl)-OH, Boc-Ser(Bzl)-OH and $CH_3COOH$. The protected thymosin $\alpha_1$-$N_{1-14}$-resin, Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(ClZ)—$OCH_2$—$C_6H_4$—resin, weighed 3.28 gm. Part of the so obtained material (1.0 gm) was mixed with 2 ml each of anisole and thioanisole and 16 ml TFA. Dry HBr gas was gently bubbled through the mixture under magnetic stirring for 60 minutes at room temperature. Evaporation of the acids and extraction of the peptide in a manner similar to that described above in Example 2 afforded 0.32 gm of crude product which on purification by preparative HPLC (polystyrene PRP-1 column, with 20% CH$_3$CN in 0.05% TFA as eluant) gave 0.21 gm of the desired thymosin $\alpha_1$-N$_{1-14}$. Its amino acid composition is Asp, 2.00; Thr, 3.17; Ser, 2.75; Glu, 0.99; Ala, 2.00; Val, 0.97; Ile, 0.94; Lys, 1.07 (hydrolysis in 6N HCl, 110° C., 24 hr). It migrated identically with the reference compound prepared by the fragment condensation method on analytical HPLC.

What is claimed is:

1. In a solid phase peptide synthesis process for producing a peptide amide having the amino acid sequence represented by the formula

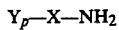

$$Y_p\text{—X—NH}_2$$

where

Y$_p$ represents the N-terminal peptide fragment, and X—NH$_2$ represents the C-terminal amino acid having an amide group (—CONH$_2$) in its molecular structure by forming the peptide having the above sequence bonded to a resin, said peptide optionally having one or more protected functional groups and cleaving the peptide from the resin and deprotecting protected functional groups;

the improvement comprising forming the peptide bonded to methylbenzhydrylamine resin and cleaving and deprotecting the resin bound peptide with hydrogen bromide.

2. The process of claim 1 wherein the peptide bonded to methylbenzhydrylamine resin is suspended in trifluoroacetic acid and anhydrous hydrogen bromide gas is blown into the suspension to effect cleavage and deprotection.

3. The process of claim 1 wherein a mixture of hydrogen bromide gas and anisole is used to effect cleavage and deprotection.

4. The method of claim 1 wherein a mixture of hydrogen bromide, anisole and thioanisole is used to effect cleavage and deprotection.

5. The method of claim 4 wherein the volume ratio of anisole to thioanisole is from about 20:80 to about 80:20.

6. The method of claim 4 wherein the volume ratio of anisole to thioanisole is about 1:1.

7. In a solid phase peptide synthesis process for producing a peptide of a desired amino acid sequence by the steps of (a) temporarily chemically protecting the reactive amino group and any other reactive groups, other than the carboxylic acid group at the alpha-position, on the C-terminal amino acid of the peptide; (b) chemically binding the protected C-terminal amino acid via the carboxylic acid (—COOH) group thereof to a resin support; (c) chemically deprotecting the reactive amino group of the resin-bound protected amino acid; (d) chemically coupling via a peptide bond the next amino acid in the desired sequence by contacting the resin-bound amino acid from step (c) with the next amino acid in the desired sequence with all of the reactive groups thereof, other than the carboxylic acid group at the alpha-position, chemically protected, in the presence of a coupling agent; (e) chemically deprotecting the reactive amino group of the coupled amino acid from step (d); (f) continuing the synthesis by repeating steps (d) and (e) with successive amino acids in the desired sequence being added one at a time until the total desired sequence of the protected peptide is built up on the resin; and (g) cleaving the protected peptide from the resin support and deprotecting protected reaction groups;

the improvement comprising
in step (g) contacting the resin bound protected peptide with a mixture of hydrogen bromide, anisole and thioanisole to simultaneously cleave the protected peptide from the resin support and remove the protecting groups.

8. The process of claim 7 wherein the anisole and thioanisole are present at a volume ratio of from about 1:4 to about 4:1.

9. The process of claim 7 wherein the anisole and thioanisole are present at a volume ratio of about 1:1.

10. The process of claim 7 wherein prior to step (g) the resin bound protected peptide is suspended in trifluoroacetic acid.

11. The process of claim 7 wherein the resin support is selected from the group consisting of chloromethylated polystyrene resin and methylbenzhydrylamine resin.

12. In a solid phase synthesis of the thymosin $\alpha_1$, polypeptide having the sequence:

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH by forming the polypeptide having the above sequence anchored to a resin, said polypeptide optionally having one or more protected functional groups; and cleaving the polypeptide from the resin and deprotecting protected functional groups of the polypeptide; the improvement comprising using methylbenzhydrylamine resin and cleaving and deprotecting the polypeptide by contacting the polypeptide with hydrogen bromide.

13. The process of claim 12 wherein the methylbenzhydrylamine resin bound polypeptide is cleaved and deprotected with a mixture of anhydrous hydrogen bromide gas in trifluoroacetic acid.

14. The process of claim 13 wherein the mixture additionally comprises anisole.

15. The process of claim 14 wherein the mixture additionally comprises thioanisole.

16. The process of claim 15 wherein the volume ratio of anisole to thioanisole is from about 1:4 to about 4:1.

17. The process of claim 15 wherein the volume ratio of anisole to thioanisole is about 1:1.

18. In a solid phase synthesis of the N-terminal 14 amino acid partial sequence of thymosin $\alpha_1$ having the following sequence:

Ac-Ser-Asp-Ala-Ala-Val-Asp-Thr-Ser-Ser-Glu-Ile-Thr-Thr-Lys-OH by forming a protected polypeptide having the above sequence anchored to a benzyl ester resin; and cleaving the polypeptide from the resin and deprotecting the polypeptide; the improvement comprising cleaving and deprotecting the polypeptide by contacting the polypeptide with a mixture of anhydrous hydrogen bromide, anisole and thioanisole.

19. The process of claim 18 wherein the volume ratio of anisole to thioanisole is from about 1:4 to about 4:1.

20. The process of claim 18 wherein the volume ratio of anisole to thioanisole is about 1:1.

21. The process of claim 18 wherein the cleavage and deprotection are carried out in trifluoroacetic acid.

* * * * *